(12) United States Patent
Zhang et al.

(10) Patent No.: US 8,805,625 B2
(45) Date of Patent: Aug. 12, 2014

(54) THREE-DIMENSIONAL VISUALIZATION AND ANALYSIS METHOD AND SYSTEM FOR NON-DESTRUCTIVE EXAMINATION OF A ROTOR BORE USING ULTRASOUND

(75) Inventors: Jingdan Zhang, Plainsboro, NJ (US); Shaohua Kevin Zhou, Plainsboro, NJ (US); Waheed A. Abbasi, Murrysville, PA (US); Chris Vierck, Oviedo, FL (US); Peter Faltin, Aachen (DE); Daniel S. Morgan, White Oak, PA (US); Larry C. Himes, Greensburg, PA (US); Dorin Comaniciu, Princeton Junction, NJ (US); Michael J. Metala, Murrysville, PA (US)

(73) Assignees: Siemens Corporation, Iselin, NJ (US); Siemens Energy, Inc., Orlando, FL (US)

( * ) Notice: Subject to any disclaimer, the term of this patent is extended or adjusted under 35 U.S.C. 154(b) by 973 days.

(21) Appl. No.: 12/903,501

(22) Filed: Oct. 13, 2010

(65) Prior Publication Data
US 2011/0087443 A1 Apr. 14, 2011

Related U.S. Application Data

(60) Provisional application No. 61/251,332, filed on Oct. 14, 2009.

(51) Int. Cl.
  *G01B 5/28* (2006.01)
  *G01N 21/88* (2006.01)
  *G01N 21/954* (2006.01)
  *G06T 17/00* (2006.01)
  *G09G 5/28* (2006.01)
  *G01N 29/44* (2006.01)
  *G01N 29/06* (2006.01)

(52) U.S. Cl.
CPC ...... *G01N 29/4463* (2013.01); *G01N 2291/101* (2013.01); *G01N 2291/2693* (2013.01); *G01N 2291/044* (2013.01); *G01N 29/0654* (2013.01)

USPC ............... 702/39; 702/34; 702/35; 702/189; 382/152; 382/154; 345/424; 345/611

(58) Field of Classification Search
CPC .......... G01N 29/0654; G01N 29/4463; G01N 2291/044; G01N 2291/101; G01N 2291/2693; G01N 29/0258; G01N 29/0672; G01C 3/00; G01H 1/003; G06F 17/5018
USPC ......... 702/34, 35, 39; 382/152, 154; 345/424, 345/611
See application file for complete search history.

(56) References Cited

U.S. PATENT DOCUMENTS

| | | | |
|---|---|---|---|
| 3,952,581 A | 4/1976 | Gottelt |
| 4,105,972 A | 8/1978 | Smith |
| 4,304,134 A | 12/1981 | Rouse et al. |

(Continued)

OTHER PUBLICATIONS

Oomes et al., 3D Shape Representation: Transforming Polygons into Voxels, Scale-Space '97 Proceedings of the First International Conference on Scale-Space Theory in Computer Vision, pp. 349-352, 1997.*

*Primary Examiner* — Janet Suglo
*Assistant Examiner* — L. Anderson (57) ABSTRACT

A method and apparatus for three-dimensional (3D) visualization and analysis for automatic non-destructive examination of a rotor bore using ultrasound. Data is acquired by scanning the rotor bore with an ultrasound pulser/transducer producing a plurality of one-dimensional ultrasound scans, each scan having a plurality of sample points. Each sample point is associated with a voxel of a regular 3D grid having a plurality of voxels. A Gaussian kernel is associated with each sample point and a value for a particular voxel is determined based on a weighted sum of sample points whose kernels cover the particular voxel. The values for the other voxels of the regular 3D grid are determined similarly. A 3D visualization of the rotor bore can be displayed to a user.

24 Claims, 9 Drawing Sheets

(56) References Cited

U.S. PATENT DOCUMENTS

| | | |
|---|---|---|
| 4,453,410 A | 6/1984 | Schmitz et al. |
| 4,751,657 A * | 6/1988 | Imam et al. .................... 702/35 |
| 5,189,915 A | 3/1993 | Reinhart et al. |
| 7,017,414 B2 | 3/2006 | Falsetti et al. |
| 2005/0022602 A1 * | 2/2005 | Falsetti et al. .................. 73/627 |
| 2012/0230566 A1 * | 9/2012 | Dean et al. .................... 382/131 |

* cited by examiner

THREE-DIMENSIONAL VISUALIZATION AND ANALYSIS METHOD AND SYSTEM FOR NON-DESTRUCTIVE EXAMINATION OF A ROTOR BORE USING ULTRASOUND

This application claims the benefit of U.S. Provisional Application No. 61/251,332, filed Oct. 14, 2009, the disclosure of which is herein incorporated by reference.

BACKGROUND OF THE INVENTION

The present invention relates to non-destructive examination of rotor bores, and more particularly, to three-dimensional visualization and analysis for automatic non-destructive examination of rotor bores using ultrasound.

A rotor is a rotating component of a turbine or a generator and rotor reliability is a major concern to turbine users such as electric utilities. To promote operational safety and prevent potential failures, Non-Destructive Examinations (NDEs) are typically performed regularly to inspect the integrity of rotors. One type of non-destructive examination is boresonic inspection in which ultrasound is used to detect defects and flaws in a rotor.

In a boresonic inspection, indications of flaws and material discontinuities, if present in the rotor, are detected using ultrasound and reported as digital data. This digital information is evaluated to determine the size and extent of defects and flaws such as material discontinuities. Performing this determination is not a trivial task and involves engineering know-how as well as experience. However, even with this know-how and experience, many assumptions are made and safety factors added in to make a representative assessment of rotor integrity. As a result, many boresonic inspection systems have a high degree of conservatism in data analysis, causing inaccurate flaw size estimation. Accordingly, a more accurate and user friendly method for boresonic inspection of rotors is desirable.

BRIEF SUMMARY OF THE INVENTION

The present invention provides a method for generating a three-dimensional visualization of a rotor bore.

In one embodiment of the present invention, a 3D visualization of a rotor bore is generated by scanning a rotor bore to generate one or more one-dimensional (1D) A-Scans. Each of a plurality of sample points of the one or more 1D A-Scans are associated with a particular voxel of a regular 3D grid comprising a plurality of voxels. A Gaussian kernel is associated with each sample point and a value for the particular voxel point is determined based on the weighted sum of sample points whose kernels cover the particular voxel. The values for each of the plurality of voxels can be determined similarly. The 3D visualization can be displayed to a user.

These and other advantages of the invention will be apparent to those of ordinary skill in the art by reference to the following detailed description and the accompanying drawings.

DETAILED DESCRIPTION

The present invention relates to a visualization and analysis method and apparatus for automatic non-destructive examination of rotor bores using ultrasound. A digital image is often composed of digital representations of one or more objects (or shapes). The digital representation of an object is often described herein in terms of identifying and manipulating objects. Such manipulations are virtual manipulations accomplished in the memory or other circuitry/hardware of a computer system. Accordingly, it is to be understood that embodiments of the present invention may be performed within a computer system using data stored within the computer system. In an ultrasonic rotor bore inspection, a large amount of data is captured. These data are manipulated to produce a three-dimensional representation in order to convey comprehensive 3D information enabling users to analyze the data efficiently and reliably. Embodiments of the present invention are described herein to provide an understanding of the visualization and analysis method and apparatus.

A rotor is the rotating part of a mechanical device. Rotors generally comprise a shaft with a plurality of blades extending radially from the shaft. Typically, a working fluid, such as air or water, may move or be moved by the rotor blades. In one application, water is directed toward the rotor blades to turn the rotor. The shaft in these types of applications is connected to an electricity producing device such as a generator.

Figure 1:
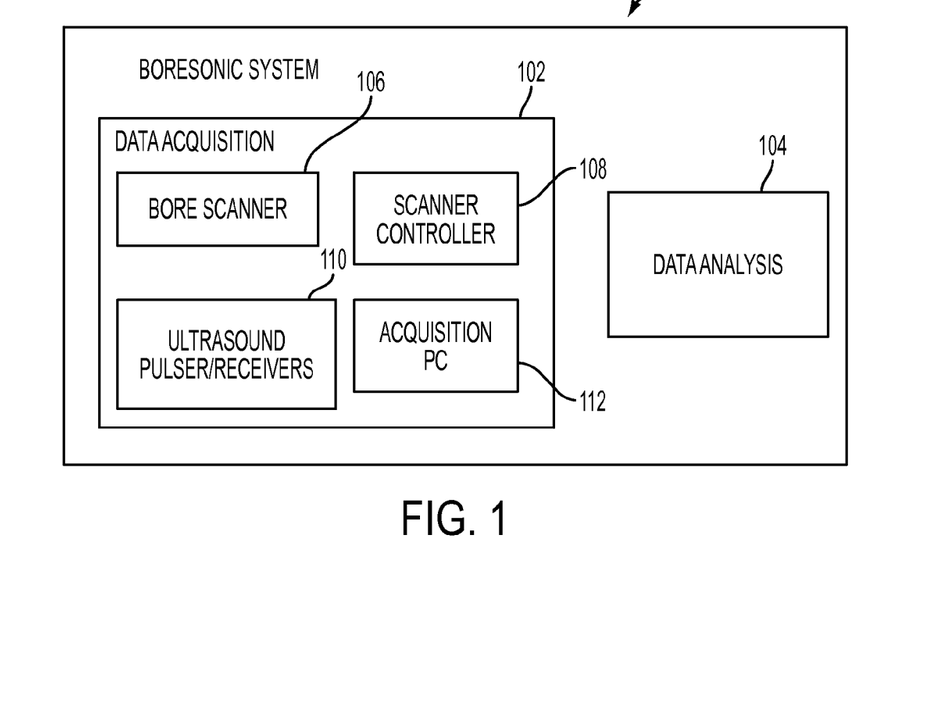
FIG. 1 illustrates a boresonic system according to an embodiment of the present invention.
Figure 2:
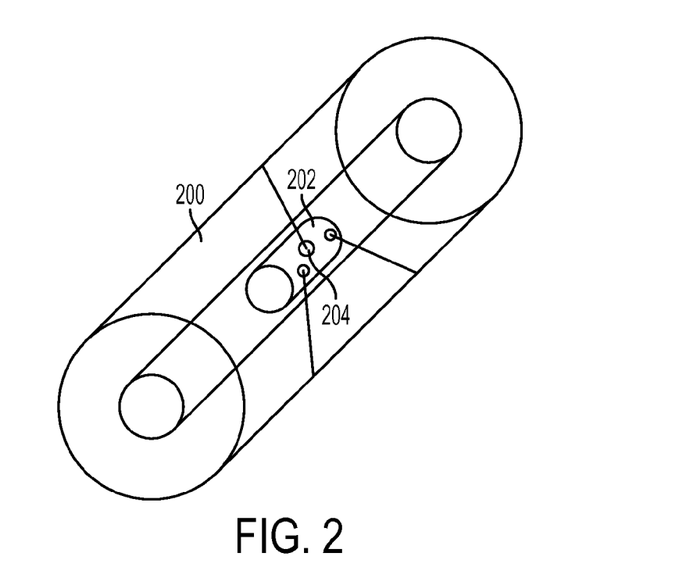
FIG. 2 illustrates a scanner having multiple transducers inserted into a rotor bore.

FIG. 1 depicts a boresonic system 100 comprised of two subsystems, namely, data acquisition subsystem 102 and data analysis subsystem 104. Data acquisition subsystem 102 scans a rotor bore and captures the ultrasonic waveforms. Data acquisition subsystem 102, in one embodiment, comprises a bore scanner 106, a scanner controller 108, ultrasound pulsers/receivers (transducers) 110, and an acquisition PC 112. FIG. 2 illustrates a bore scanner 202 having multiple ultrasonic transducers 204 inserted into rotor 200. Referring to FIGS. 1 and 2, in an exemplary data acquisition procedure, bore scanner 106 is controlled by scanner controller 108 and data acquisition PC 112 to automatically scan the bore area of a rotor, such as rotor 200 shown in FIG. 2. While scanning, the raw ultrasonic waveform is sent and received by each transducer and the received signal is digitized and stored by data acquisition PC 112. In one embodiment, the captured scans are one dimensional (1D) signals, referred to as A-scan signals are stored in an RDTiff format file as a channel.

Boresonic systems may have a variety of different features. In one embodiment, a helical scanner with high mechanical precision is used to capture data with high spatial resolution. Multiple transducers 204 with different frequencies and wave modes may be used in one embodiment to detect flaws with different reflection properties and at different depths.

Figure 3:
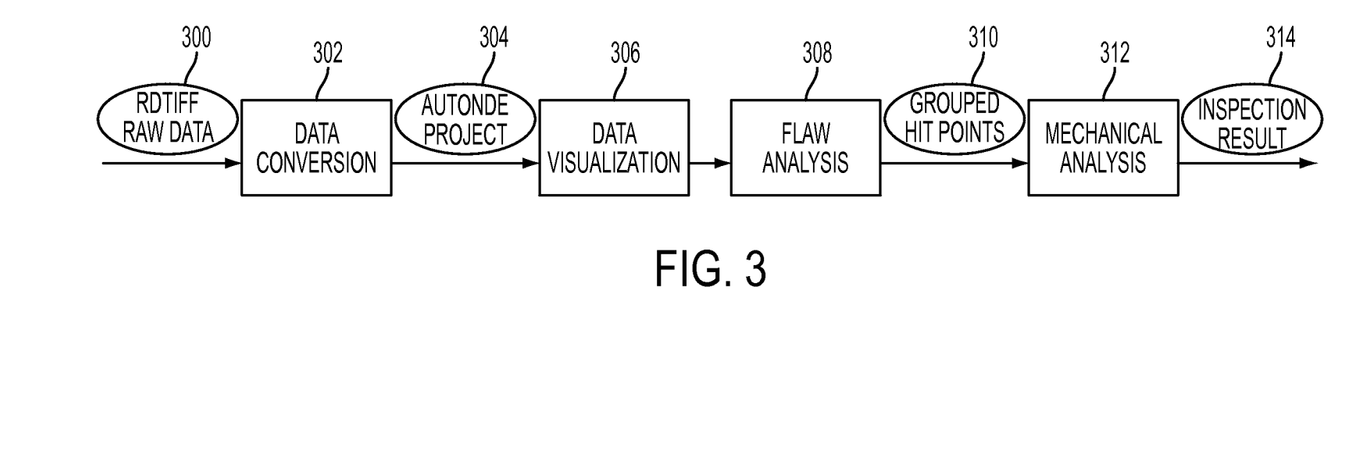
FIG. 3 illustrates an automatic non-destructive examination rotor bore system according to one embodiment of the invention.

FIG. 3 depicts an Automatic Non-Destructive Examination Rotor Bore (AutoNDE-RB) system according to one embodiment of the invention. The AutoNDE-RB represents and renders captured 1D data representing a rotor bore as 3D volumes. The captured A-Scan signals are converted to 3D volumes which may be viewed directly in 3D space. A set of 3D manipulation functions are provided, such as translation, rotation, zoom to region of interest, and Multi-Planar Reformatting (MPR). Further, AutoNDE-RB can render detail appearance of a flaw by converting the captured data in a region of interest to a high resolution volume. AutoNDE-RB integrates information from different channels. The data in different channels can be viewed jointly by fusing these data with different approaches. This functionality enables users to easily verify indications across different channels to better understand the characteristics of a flaw. AutoNDE-RB supports 3D CAD model rendering. By overlaying a CAD model with 3D volumes, engineers can easily identify geometric noise caused by the rotor geometry and distinguish geometric noise from actual flaws. AutoNDE-RB is an integrated platform to visualize and analyze the NDE data. AutoNDE-RB provides features to convert 3D data, visualize captured data and CAD models, measure the flaw size, reduce geometric noise, compute hitpoints from reflection signals, and group hitpoints to flaws. In one embodiment, all these features are supported by a unified graphic interface.

As shown in FIG. 3, the AutoNDE-RB is comprised of three modules: a data conversion module 302, data visualization module 306, and a flaw analysis module 308. Also shown in FIG. 3 is mechanical analysis module 312 which applies fracture mechanics to deterministically calculate remaining rotor bore life in cycles.

As described above, captured 1D A-scans may be stored as RDTiff files 300. These RDTiff files 300 are converted, in one embodiment, by data conversion module 302 to AutoNDE-RB project 304 which is a file format of the AutoNDE-RB system. In one embodiment, the AutoNDE-RB project contains raw A-Scan data, volumetric data reconstructed from the A-Scan data, and the text description of the inspection.

Data visualization module 306 is adapted to manipulate the data contained in AutoNDE-RB project 304 to visualize a three dimensional (3D) volume representing the rotor bore based on the A-Scan data stored in the AutoNDE-RB project. Data visualization module 306, in one embodiment, is adapted to allow the 3D volumes to be visualized using a volume rendering technique or in two dimensions (2D) as cutting slices. The data visualization module allows users, such as engineers, to manipulate the volumes in order to identify flaws and check the flaw appearance in each channel. In one embodiment, a region may be analyzed with high accuracy by selecting a region of interest (ROI) and reconstructing a high resolution volume in the selected ROI.

Flaw analysis module 308 is adapted to compute hitpoints, each of which is a flaw indication (e.g. a material discontinuity). Some of these hit points may correspond to geometric noise. Hit points corresponding to geometric noise, in one embodiment, may be removed automatically upon detection by the flaw analysis module. In another embodiment, hit points corresponding to geometric noise may be removed from the 3D volume manually.

Flaw analysis module 308 is adapted to group the remaining hitpoints to flaws based on their spatial proximity to one another and data acquisition parameters. Flaw analysis module 308 is further adapted to output grouped hitpoints 310. In one embodiment, the hit points and grouping results can be overlaid with volume data to verify the computation results.

Mechanical analysis module 312 is adapted to evaluate grouped hitpoints 310 using fracture mechanics methodology to deterministically calculate the remaining life in cycles of the rotor. Inspection result 314 is output from mechanical analysis module 312.

Figure 4:
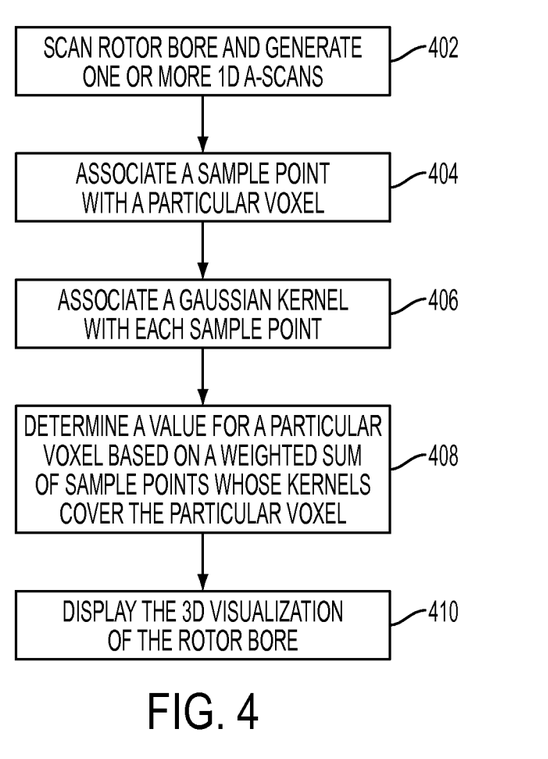
FIG. 4 illustrates a method to convert acquired A-Scan ultrasound data to a 3D volume for visualization according to one embodiment.

FIG. 4 depicts a method for 3D volume reconstruction according to one embodiment of the invention. At step 402 the rotor bore is scanned to generate raw inspection data (one-dimensional (1D) A-Scans) stored as RDTiff files. For example, the raw inspection data can be acquired using a scanning system, such as a SIEMENS SIEBOR Boresonic system designed by SEIMENS PG, Penn Hall, which automatically captures ultrasound reflection signals on rotor bores. The scanning system may have multiple ultrasonic search units mounted on the scan head. Each search unit is a pulser/receiver transducer configured to send and receive an ultrasound waveform with a specific wave mode (longitudinal or shear wave mode), frequency, incidence angle, and depth range (e.g. FIG. 2 depicts scanner 202 having multiple pulser/receiver transducers 204). The data received by transducer 204 reveal flaws at specific depths with specific reflection properties. The data from each transducer may be stored as a channel in RDTiff files.

It should be noted that, in one embodiment, scanner 202 of FIG. 2 performs a helical scan movement to capture reflection information in multiple channels. At each scan position, an A-Scan signal is recorded in each channel. The 3D configuration of an A-Scan line can be determined by the scan parameters. The combination of all A-Scans provides a dense sampling in the 3D space near the bore space.

Figure 5:
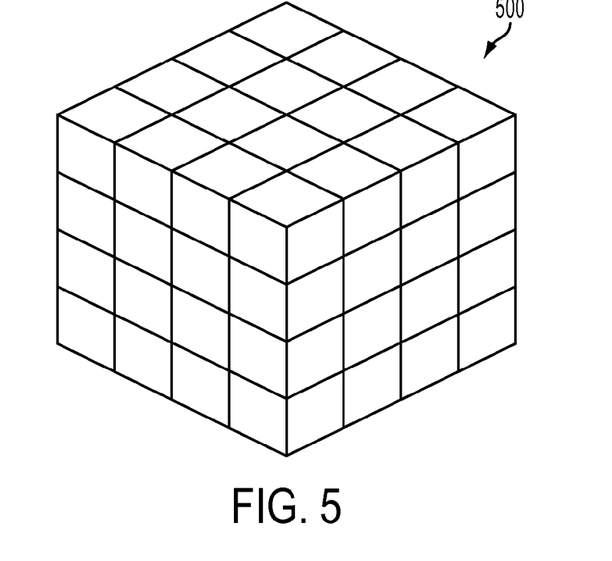
FIG. 5 illustrates a regular three-dimensional grid.

Rendering a volume in real time enables a user to manipulate and analyze data efficiently. In order to achieve this, the volume is represented in a regular grid 500 as shown in FIG. 5. Since the sampling points of the A-Scan data are distributed irregularly, the raw A-Scan data stored in RDTiff files is typically not used directly for 3D volume rendering. In step 404, a sample point of an A-Scan is associated with a voxel on regular grid 500 of FIG. 5. In step 406, a Gaussian Kernel is associated with the sample point.

Figure 6A:
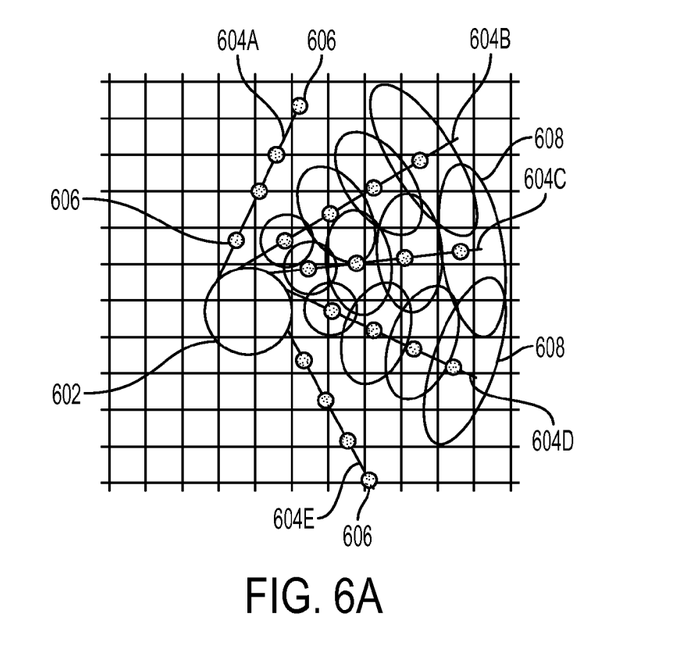
FIG. 6A illustrates associating a sample point with a point on regular three-dimensional grid.

FIG. 6A illustrates associating a sample point with a point on regular grid 500 and associating the same sample point with a Gaussian kernel. Circle 602 of FIG. 6A represents a bore surface which, in this example, is the interior surface of rotor 200 of FIG. 2. Lines 604A-604E originating from circle 602 represent A-Scans having multiple sampling points 606 along their lengths. The circles and ovals surrounding each sample point represent a Gaussian kernel 608 associated with each sample point.

In one embodiment, an algorithm named Spatially Adaptive Gaussian Reconstruction (SAGR) uses Gaussian kernels to reconstruct 3D volumes represented by A-Scans to a regular grid (e.g. grid 500 of FIG. 5). The Gaussian kernel associated with each sample point controls the range and magnitude of the sampling point's contribution to its nearby grid points. The size and shape of the Gaussian Kernel is, in one embodiment, balanced by two factors. To prevent sampling aliasing, a kernel should be big enough to cover its nearby grid points. To prevent over blurring, the overlapping among neighboring kernels should be minimized. As a result, in one embodiment, the shape and size of a kernel are determined by one or more of the local sampling pattern, the local sampling density, and the resolution of the regular grid.

Figure 6B:
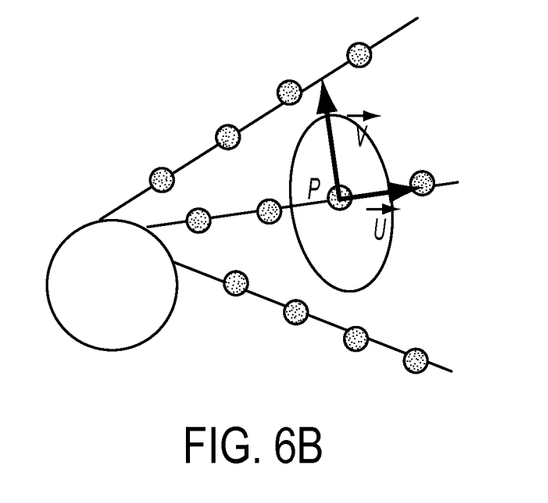
FIG. 6B illustrates determining the orientation and size of a kernel according to one embodiment.
Figure 6C:
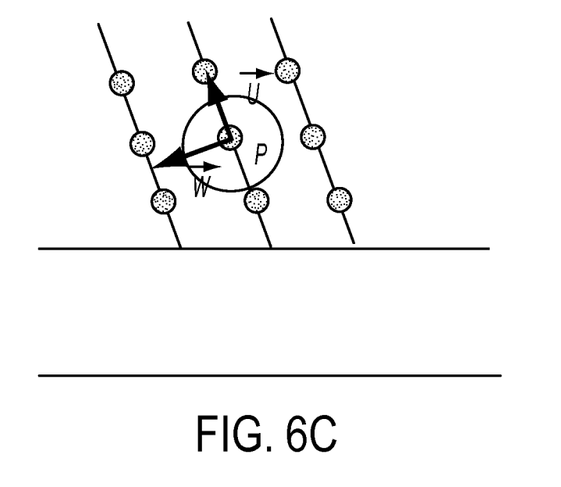
FIG. 6C illustrates variables used in determining the orientation and size of a kernel according to one embodiment.

FIGS. 6B and 6C illustrate how the size and orientation of a kernel is determined. FIG. 6B depicts a X-Y rotor bore view in which A-Scan sweeping direction is clockwise. FIG. 6C depicts a X-Z rotor bore axial view in which the axial moving direction is from left to right. A kernel is a 3D Gaussian function defined within a 3D ellipsoid. The kernel's orientation and size at a sampling point P are computed as follows.

First, the kernel orientation is determined. Referring to FIGS. 6B and 6C, the kernel orientation is defined by three orthogonal vectors ($\vec{U}$, $\vec{V}$, $\vec{W}$), where $\vec{U}$ is the A-Scan line direction; $\vec{W}$ is the normal of the A-Scan sweeping plane; and $\vec{V}$ is the cross product of $\vec{W}$ and $\vec{U}$.

Next, the lengths of the vectors are determined. The length $\|\vec{U}\|$ is the distance between the point P to its adjacent point on the same A-Scan. The length $\|\vec{V}\|$ the distance of the point P to the previous A-Scan along the $\vec{V}$ direction. The length $\|\vec{W}\|$ is the distance of the point P to the previous sweeping plane along the $\vec{W}$ direction.

The size of the kernel is then determined. The radiuses ($r_u$, $r_v$, $r_w$) of the kernel along $\vec{U}$, $\vec{V}$, and $\vec{W}$ are determined as $r_u = \max(\alpha \|\vec{U}\|, L)$, $r_v = \max(\alpha \|\vec{V}\|, L)$, and $r_w = \max(\alpha \|\vec{W}\|, L)$ respectively, where $\alpha$ is a predefined constant and L is the resolution of the 3D grid. In order to avoid aliasing, the radius of the kernel should not less than the 3D grid resolution L. In one embodiment, $\alpha$ is set to 0.7.

Finally, the corresponding Gaussian function is determined. The variance ($\sigma_u$, $\sigma_v$, $\sigma_w$) along $\vec{U}$, $\vec{V}$, and $\vec{W}$ are determined as $\sigma_u = \beta r_u$, $\sigma_v = \beta r_v$, and $\sigma_w = \beta r_w$ respectively, where $\beta$ is a predefined constant. In one embodiment, $\beta = 0.3$.

Returning to FIG. 4, at step 408, a value for a particular voxel (volume pixel) of grid 500 is determined based on a weighted sum of sample points whose kernels cover the particular voxel.

The process is repeated for each voxel of the 3D grid to produce a 3D representation of a desired segment or section of a rotor (e.g. rotor 200 of FIG. 2). Since, in one embodiment, each channel has a different incident angle and sampling pattern, a volume for each channel is constructed separately and kernel size and shape are based on the specific sampling pattern of the channel. In reconstruction, forward mapping is applied. In forward mapping, the footprint of each sample point on the grid is determined. Then the voxel value is computed as a weighted sum of all footprints covering the voxel for which the value is being computed.

Figure 7:
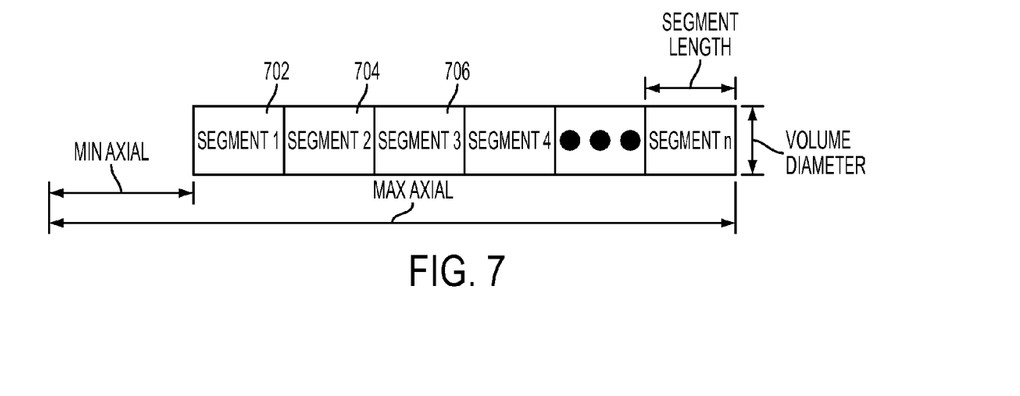
FIG. 7 illustrates a data storage format in which an overall volume of a rotor bore is divided into segments.

The amount of data representing a rotor bore can be large which, in turn, may take a long time to convert for a 3D representation. Further, the amount of data an entire rotor bore for a 3D representation may be large. The data representing an entire rotor bore may be divided into smaller segments. FIG. 7 illustrates how an overall volume representing the rotor bore may be stored as segments. In one embodiment as shown in FIG. 7, the data representing an overall volume of a rotor bore may be divided into segments (e.g. segments 702, 704, 706, etc.) with each segment covering an axial range of the rotor bore.

Figure 8:
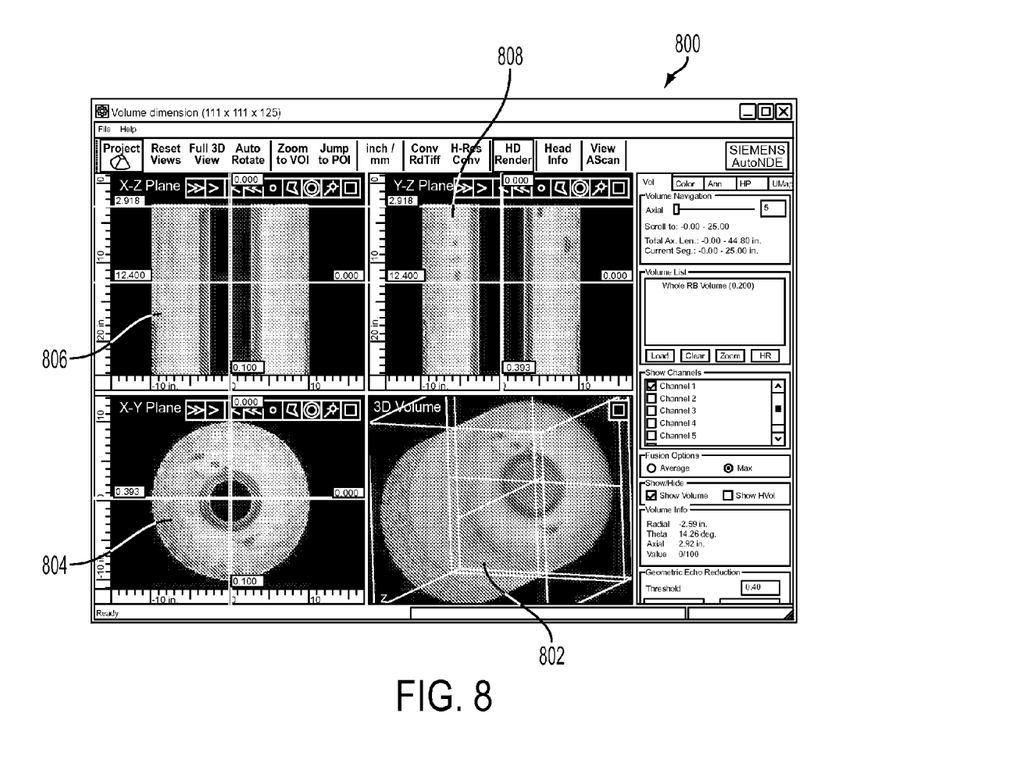
FIG. 8 illustrates a graphical user interface (GUI) according to one embodiment of the invention.

After data conversion, at step 410 of FIG. 4, a 3D representation of the rotor bore is visualized by data visualization module 306 (shown in FIG. 2). Data visualization module 306 is used to display the 3D representation and allows a user to visually analyze the converted data. For example, the 3D representation of the rotor bore can be visualized by a graphical user interface. FIG. 8 depicts a Graphic User Interface (GUI) 800 according to one embodiment. AutoNDE-RB provides the following visualization functions.

3D volume rendering visualizes a volume reconstructed from the raw A-Scan data as shown in the lower right pane 802 of GUI 800. This 3D visualization enables a user to effectively identify potential flaws and analyze the 3D geometry and appearance of the flaws. In visualization, a volume can be interactively rotated, translated, and zoomed in and out.

Multi Planar Reformatting (MPR) may be applied to display 2D slices of a volume as shown in panes 804, 806, and 808 which are illustrated displaying 2D slices on orthogonal cutting planes (x-z, y-z, and x-y). The positions of the cutting planes can be interactively adjusted by a user.

On-screen measurement is provided in MPR planes via the use of rulers and cursors enabling a user to measure the size of flaws as well as other aspects of images. In one embodiment, the coordinate system used by the on-screen rulers is consistent with the coordinate system of data acquisition subsystem 102.

Figure 9:
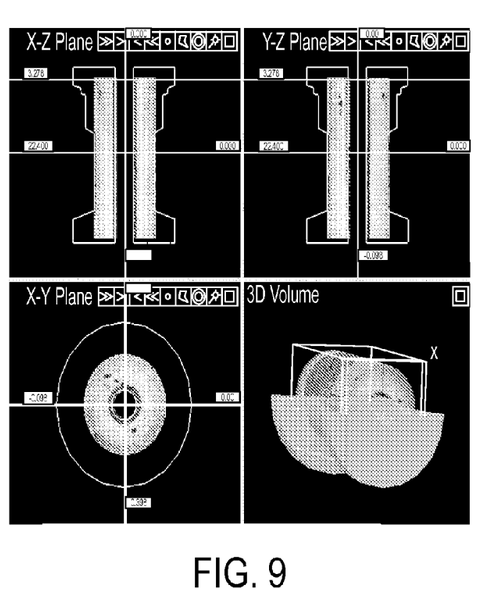
FIG. 9 illustrates Computer Aided Drafting (CAD) models of a rotor bore overlaying a volume.

FIG. 9 illustrates a CAD model of a rotor bore overlaying a reconstructed volume depicting a rotor bore. Overlaying as shown in FIG. 9 allows a user to view a volume overlaying a CAD model. Where CAD models of the inspected component are available, AutoNDE-RB can give a 3D reference of the captured data by overlaying the CAD model with the volume in both MPR and volume rendering.

Figure 10A:
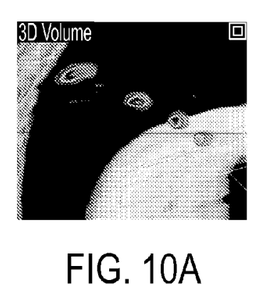
FIG. 10 illustrates fusing of multiple channels.
Figure 10B:
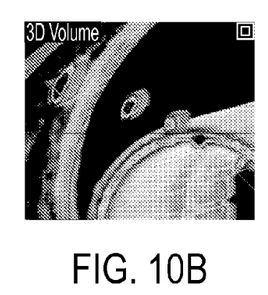
Figure 10C:
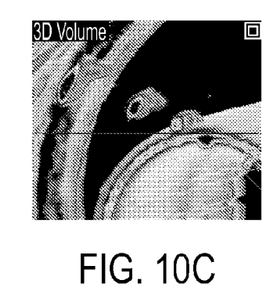

Channel fusion allows a user to view multiple channels jointly. FIG. 10 illustrates channel A shown in FIG. 10 image A and channel B shown in FIG. 10 image B fused to channel C as shown in FIG. 10 image C. In one embodiment, the average or maximum fusion strategy may be used.

Figure 11:
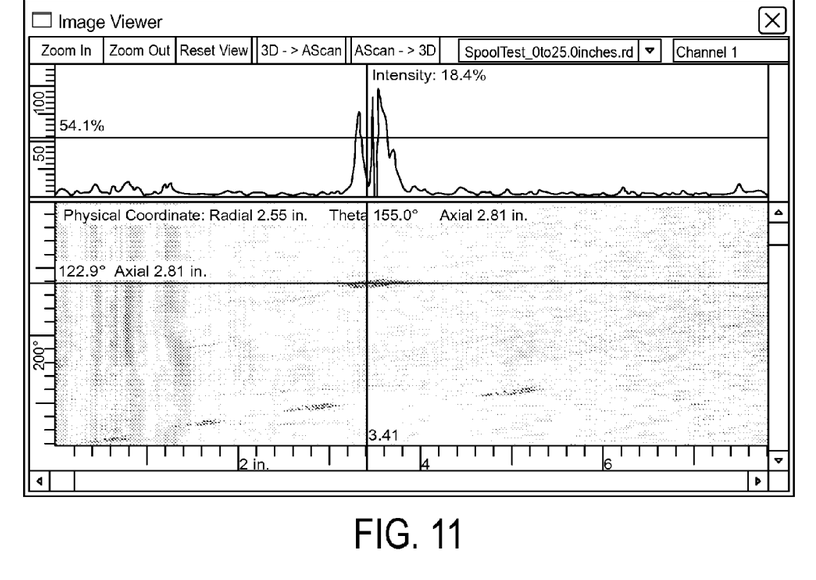
FIG. 11 illustrates A-Scan data displayed as a 1D plot and a 2D image.

FIG. 11 illustrates A-Scan data displayed as a 1D plot and a 2D image. A-Scan visualization as shown in FIG. 11 is provided in one embodiment allowing a user to view the raw A-Scan data as 1D or 2D images. In one embodiment, the A-Scan view and 3D view are linked allowing a user to select a 3D position in the 3D view and check the related A-Scans.

Figure 12A:
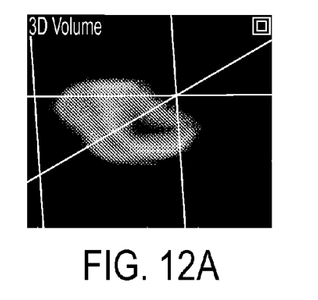
FIG. 12 illustrates a high resolution volume reconstruction of a user identified region of interest.
Figure 12B:
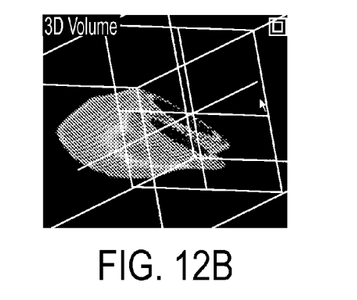

Zoom to a region of interest (ROI) allows a user to view regions containing potential flaws for better visualization. FIG. 12 image B depicts a high resolution volume reconstructed based on the region of interest identified by a user as shown in FIG. 12 image A.

Figure 13A:
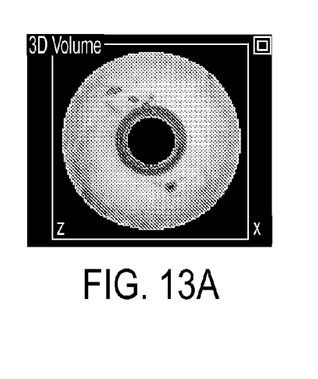
FIG. 13 illustrates a cross section of a rotor volume before and after application of circular geometric noise reduction (CEGR)
Figure 13B:
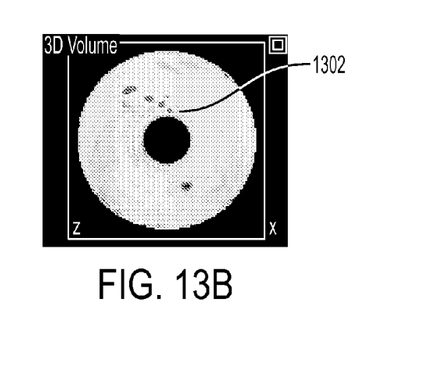

Circular geometric echo reduction (CEGR) is used in one embodiment to reduce the geometric echo noise usually mixed with a flaw reflection signal. FIG. 13A depicts a cross section of a rotor prior to CEGR being applied having geometric echo noise appearing as a circle with the center at the axis of the rotor. As shown in FIG. 13 image B, the geometric echo noise is reduced by subtracting the mean intensity of the circle from each voxel on the circle. Flaw 1302, previously obscured by the geometric echo noise in FIG. 13 image A is now more clearly visible in FIG. 13 image B. In other embodiments, the geometric echo noise may be reduced manually by a user.

In boresonic flaw analysis, the potential flaws are identified and also evaluated to predict the remaining life of a rotor. In one embodiment, WESTINGHOUSE ELECTRIC Rotor Life Evaluation (WEROLE) is used for evaluation. WEROLE computes the cyclic life of a rotor by analyzing the rotor under various simulated operation conditions using fracture mechanics methodology. The input of WEROLE is the grouped indication of flaws from data visualization module 306.

AutoNDE-RB flaw analysis module computes hit points form captured data. Each hitpoint represents an indication whose intensity magnitude is larger than a predefined threshold. The size of a hitpoint, in one embodiment, is determined based on a Distance Gain Sizing (DGS) method. AutoNDE-RB, in one embodiment, provides a set of tools for allowing users to remove hit points computed form geometric echo noise. A grouping program is called by AutoNDE-RB to combine the hit points into flaws based on their spatial proximity to one another and the data acquisition parameters. In one embodiment, the grouping program ultrasound Mapping and Analysis Program (UMAP) is used to combine the hit points into flaws as described. In one embodiment, the grouped hit points may be visualized with the related 3D volume to validate the result.

Figure 14:
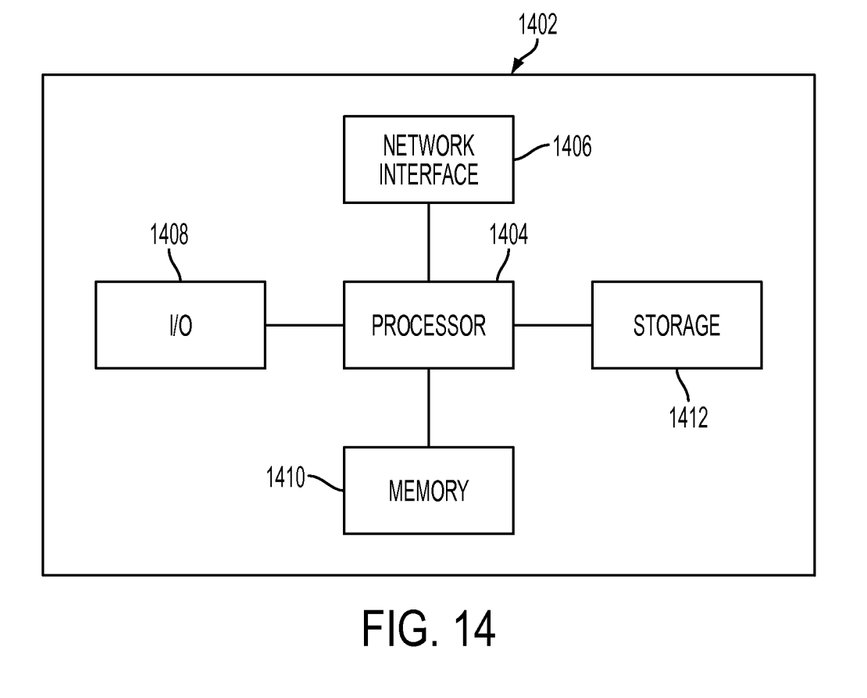
FIG. 14 is a high level block diagram of a computer capable of implementing the present invention.

The above-described methods for 3D rotor bore visualization and analysis may be implemented on a computer using well-known computer processors, memory units, storage devices, computer software, and other components. A high level block diagram of such a computer is illustrated in FIG. 14. Computer 1402 contains a processor 1404 which controls the overall operation of the computer 1402 by executing computer program instructions which define such operation. The computer program instructions may be stored in a storage device 1412, or other computer readable medium, (e.g., magnetic disk) and loaded into memory 1410 when execution of the computer program instructions is desired. Thus, all method steps described above, including the method steps illustrated in FIG. 4, may be defined by the computer program instructions stored in the memory 1410 and/or storage 1412 and controlled by the processor 1404 executing the computer program instructions. The computer 1402 also includes one or more network interfaces 1406 for communicating with other devices via a network. The computer 1402 also includes other input/output devices 1408 that enable user interaction with the computer 1402 (e.g., display, keyboard, mouse, speakers, buttons, etc.) One skilled in the art will recognize that an implementation of an actual computer could contain other components as well, and that FIG. 14 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for generating a three-dimensional (3D) visualization of a rotor comprising:
associating, by a processor, each of a plurality of sample points of one or more one dimensional (1D) A-Scans of the rotor with a particular voxel of a regular three-dimensional grid comprising a plurality of voxels;
associating, by the processor, a Gaussian kernel with each sample point; and
generating, by the processor, the 3D visualization of the rotor based on the plurality of voxels by determining a value for each of the plurality of voxels based on a weighted sum of sample points whose kernels cover each particular voxel.

2. The method of claim 1 further comprising:
repeating the determining step for each of the plurality of voxels of the regular 3D grid.

3. The method of claim 1 wherein the Gaussian kernel has a shape and a size based on a local sampling pattern, a local sampling density, and a resolution of the three dimensional grid.

4. The method of claim 1 further comprising:
generating the one or more 1D A-scans representing the rotor using one or more transducers inserted into the rotor, each 1D A-Scan comprising a plurality of sampling points.

5. The method of claim 4 wherein the step of generating comprises scanning the rotor helically.

6. The method of claim 4 wherein each of the one or more transducers is arranged to emit pulses at radial angles different from each other.

7. The method of claim 1 further comprising:
displaying the 3D visualization of the rotor.

8. The method of claim 7 wherein the step of displaying further comprises displaying two-dimensional (2D) slices of the rotor generated using multi planar reformatting.

9. An apparatus for generating a three-dimensional (3D) visualization of a rotor comprising:
means for associating each of a plurality of sample points of one or more one dimensional (1D) A-Scans of the rotor with a particular voxel of a regular three-dimensional grid comprising a plurality of voxels;
means for associating a Gaussian kernel with each sample point; and
means for generating the 3D visualization of the rotor based on the plurality of voxels by determining a value for a particular one of the plurality of voxels based on a weighted sum of sample points whose kernels cover each particular voxel.

10. The apparatus of claim 9 further comprising:
means for repeating the determining step for each of the plurality of voxels of the regular 3D grid.

11. The apparatus of claim 9 wherein the Gaussian kernel has a shape and a size based on a local sampling pattern, a local sampling density, and a resolution of the three dimensional grid.

12. The apparatus of claim 9 further comprising:
generating the one or more 1D A-scans representing the rotor using one or more transducers inserted into the rotor, each 1D A-Scan comprising a plurality of sampling points.

13. The apparatus of claim 12 wherein the step of generating comprises scanning the rotor helically.

14. The apparatus of claim 12 wherein each of the one or more transducers is arranged to emit pulses at radial angles different from each other.

15. The apparatus of claim 9 further comprising:
displaying the 3D visualization of the rotor.

16. The apparatus of claim 15 wherein the step of displaying further comprises displaying two-dimensional (2D) slices of the rotor generated using multi planar reformatting.

17. A non-transitory computer readable medium encoded with computer executable instructions for performing a method for generating a three-dimensional (3D) visualization of a rotor, the computer executable instructions defining steps comprising:

associating each of a plurality of sample points of one or more one dimensional (1D) A-Scans of the rotor with a particular voxel of a regular three-dimensional grid comprising a plurality of voxels;

associating a Gaussian kernel with each sample point; and generating the 3D visualization of the rotor based on the plurality of voxels by determining a value for a particular one of the plurality of voxels based on a weighted sum of sample points whose kernels cover each particular voxel.

18. The non-transitory computer readable medium of claim 17 further comprising computer executable instructions defining the step of:

repeating the determining step for each of the plurality of voxels of the regular 3D grid.

19. The non-transitory computer readable medium of claim 17 wherein the Gaussian kernel has a shape and a size based on a local sampling pattern, a local sampling density, and a resolution of the three dimensional grid.

20. The non-transitory computer readable medium of claim 17 further comprising computer executable instructions defining the step of:

generating the one or more 1D A-scans representing the rotor using one or more transducers inserted into the rotor, each 1D A-Scan comprising a plurality of sampling points.

21. The non-transitory computer readable medium of claim 20 wherein the computer executable instructions defining the step of generating comprises scanning the rotor helically.

22. The non-transitory computer readable medium of claim 20 wherein each of the one or more transducers is arranged to emit pulses at radial angles different from each other.

23. The non-transitory computer readable medium of claim 17 further comprising computer executable instructions defining the step of:

displaying the 3D visualization of the rotor.

24. The non-transitory computer readable medium of claim 23 wherein the step of displaying further comprises displaying two-dimensional (2D) slices of the rotor generated using multi planar reformatting.

* * * * *